US006656463B2

(12) United States Patent
Harris et al.

(10) Patent No.: US 6,656,463 B2
(45) Date of Patent: Dec. 2, 2003

(54) COMPOSITIONS AND METHODS FOR REDUCING THE AMOUNT OF SALMONELLA IN LIVESTOCK

(75) Inventors: Delbert L. Harris, Ames, IA (US); Nakhyung Lee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/986,419

(22) Filed: Nov. 8, 2001

(65) Prior Publication Data

US 2002/0127207 A1 Sep. 12, 2002

Related U.S. Application Data

(60) Provisional application No. 60/246,972, filed on Nov. 13, 2000.

(51) Int. Cl.[7] .............................................. A01N 63/00
(52) U.S. Cl. .................. 424/93.6; 424/93.3; 435/235.1; 435/239
(58) Field of Search .............................. 435/235.1, 239; 424/93.3, 93.6; 422/26, 32

(56) References Cited

U.S. PATENT DOCUMENTS

| 5,811,093 | A |   | 9/1998  | Merril et al. |           |
|-----------|---|---|---------|---------------|-----------|
| 6,121,036 | A | * | 9/2000  | Ghanbari et al. | 435/235.1 |
| 6,322,783 | B1| * | 11/2001 | Takahashi     | 424/93.6  |

FOREIGN PATENT DOCUMENTS

WO 98/08944 * 3/1998

OTHER PUBLICATIONS

Barrow, P.A.—"The use of bacteriophages for treatment and prevention of bacterial disease in animals and animal models of human infection, " Journal of Chemical Technology and Biotechnology 76 (2001), pp. 677–682.

Cerveny, Karen E. et al. —"Phage Therapy of Local and Systemic Disease Caused by *Vibrio vulnificus* in Iron–Dextran–Treated Mice, " Infection and Immunity, vol. 70, No. 11, Nov. 2002, pp. 6251–6262.

Huff, W.E., et al. —Prevention of *Escherichia coli* Respiratory Infection in Broiler Chickens with Bacteriophage (SPR02)[1], Environment and Health, pp. 437–441.

Jofre, J. et al. —"Potential Usefulness of Bacteriophages That Infect *Bacteriodes fragilis* as Model Organisms for Monitoring Virus Removal in Drinking Water Treatment Plants, " Applied and Environmental Microbiology, Sep. 1995, pp. 3227–3231.

Kallings, L.O. et al. —"Resistance to Felix 0–1 Phage in Salmonella Bacteria, " The Bacteriological Department, The National Bacteriological Laboratory, Stockholm, Sweden, 1967, pp. 455–460.

Levin, Bruce R., et al.—"Phage Therapy Revisited: The Population Biology of a Bacterial Infection and its Treatment With Bacteriophage and Antibiotics, " The American Naturalist, vol. 147, No. 6, Jun. 1996, pp. 881–898.

Matsuzaki, Shigenobu, et al.—"Experimental Protection of Mice against Lethal *Staphylococcus aureus* Infection by Novel Bacteriophage φMR11," S. aureus–Specific Phage Therapy, JID 2003:187 (Feb. 15), pp. 613–624.

Murthy, Kishore et al. —"Phage therapy: an innovative approach to treat antibiotic–resistant Bacterial infections, " American Association of Swine Veterinarians, 2002, pp. 217–220.

Park, Se Chang et al. —"Isolation of Bacteriophages Specific to a Fish Pathogen, *Pseudomonas plecoglossicida*, as a Candidate, " Applied and Environmental Microbiology, Apr. 2000, vol. 66, No. 4, pp. 1416–1422.

Reynaud, A. et al. —"Characteristics and diffusion in the rabbit of a phage for *Escherichia coli* 0103, Attempts to use this phage for therapy, " Veterinary Microbiology, 30 (1992) pp. 203–212.

Sklar, I.B. et al.—"Attempts To Utilize Bacteriophage To Combat *Salmonella Enterica* Serovar Enteritidis infection in Chickens, " Journal of Food Safety 21 (2001) pp. 15–29.

Soothill, J.S. et al. —"The efficacy of phages in the prevention of the destruction of pig skin in vitro by *Pseudomonas aeruginosa*, " Med. Sci. Res. 1988, 16, pp. 1287–1288.

Williams Smith, H. et al. —"Successful Treatment of Experimental *Escherichia coli* Infections in Mice Using Phage: Its General Superiority over Antibiotics," journal of General Microbiology (1982), 128, pp. 307–318.

International Search Report dated Nov. 6, 2002.

Alisky, J., et al., "Bacteriophages Show Promise as Antimicrobial Agents, " Journal of Infection 36:5–15, 1998.

Barrow, P., et al., Use of Lytic Bactiophage for Control of Experimental *Escherichia coli* Septicemia and Meningitis in Chickens and Calves. Clinical and Diagnostic Laboratory Immunology 5/1998, pp. 294–298.

Barrow, P., et al. "Bacteriophage therapy and prophylaxis: rediscovery and renewed assessment of potential," Trends in Microbiology, vol. 5, No. 7, pp. 268–271, Jul. 1997.

Baum, D. H., et al. "Epidermiologic Studies of *Salmonella* in Swine Using Culture and Elisa, " Proceed. of Second International Symposium on Epidemiology and Control of Salmonella in Pork. Copenhagen Denmark, pp. 209–211, Aug. 1997.

Berends, B. R., et al., "Identification and quantification of risk factors in animal management and transport regarding *Salmonella* spp. in pigs," Elsevier Science B.V. 1996, pp. 37–53.jf124c Primary Examiner—Jeffrey Stucker
(74) Attorney, Agent, or Firm—Dickstein Shapiro Morin & Oshinsky LLP

(57) ABSTRACT

The invention provides compositions comprising Felix 0-1 Phage (F01 phage) in a an-acceptable carrier and methods of administering the compositions to a livestock animal to reduce or prevent dissemination of Salmonella.

28 Claims, 6 Drawing Sheets

OTHER PUBLICATIONS

Blaha, T., "*Salmonella's* Impact on Pork Production," National Hog Farmer, 30:S1–S6, Apr. 1, 2000.

Carlton, R. M., "Phage Therapy: Past History and Future Prospects," Archivum Immunologiae et Therapiae Experimentalis, 1999, 47, pp. 267–274.

Childers, A. B., et al. "Reduction of *Salmonella* and Fecal Contamination of Pork During Swine Slaughter," vol. 11, pp. 1161–1164, 1977.

Childers, A. B., "Sources of *Salmonellae* Contamination of Meat Following Approved Livestock Slaughtering Procedures," J. Milk Food Technol., vol. 36, No. 12, pp. 635–638, 1973.

Contag, C. H., Use of Bacteriophage in the Study of Staphylococcic Bovine Mastitis. M. S. Thesis, Iowa State University, 1956.

DeJong, H., et al., "Salmonellosis in Calves—The Effect of Dose Rate and Other Factors on Transmission," New Zealand Veterinary Journal, vol. 13, pp. 59–64, 1965.

Fedorka–Cray, P. J., et al. "Alternative Routes of Invasion May Affect Pathogenesis of *Salmonella typhimurium* in Swine," Infection and Immunity, vol. 63, No. 7, pp. 2658–2664, Jul. 1995.

Galton, M. M., et al. "*Salmonella* in Swine, Cattle and the Environment of Abbatoirs, " Journal of Infectious Diseases, vol. 95, pp. 236–245, 1954.

Ho, K. "Bacteriophage Therapy for Bacterial Infections," Perspectives in Biology and Medicine, vol. 44, pp. 1–16, (winter 2001).

Huovinen, P. "Bacteriotherapy: the time has come," Antimicrobial Research Laboratory, National Public Health Institute, 20520 Turku, Finland. BMJ vol. 323 Aug. 18, 2001, pp. 353–354.

Hurd, H. S., et al. "The Effect of Transport and Lairage on *Salmonella* Isolation from Market Pigs," American Assoc. of Swine Practitioners, 2000, pp. 429–434.

Kallings, L. O. "Sensitivity of various *Salmonella* Strains to Felix 0–1 Phage," Acta Pathol. et Microbiol. Scandinav. 70, pp. 446–454, 1967.

Lindberg, A. A., et al. "Influence of O Side Chains on the Attachment of the Felix 0–1 Bacteriophage to *Salmonella* Bacteria, " Journal of Bacteriology, 99, pp. 513–519, Aug. 1969.

Lindberg, A. A., et al. "Bacteriophage Attachment Sites, Serological Specificity and Chemical Composition of the Lipopolysaccharides of Semirough and Rough Mutants of *Salmonella typhimuruim*," Journal of Bacteriology, 105, pp. 57–64, Jan. 1971.

Marks, T., et al. "Bacteriophages and biotechnology: a review," J. Chem. Technol. Biotechnol., 75:6–17 (2000).

McDonagh, V. P., "The Significance of the Abottoir in *Salmonella* Infection in Bradford," J. Hyg. 56:271–179, 1958.

Modi, R., et al., "Effect of Phage on Survival of *Salmonella* Enteritidis during Manufacture and Storage of Cheddar Cheese Made from Raw and Pasturized Milk," Journal of Food Protection, vol. 64, No. 7, pp. 927–933, 2001.

Nelson, F., et al. "Prevention and elimination of upper respiratory colonization of mice by group A *streptococci* by using a Bacteriophage lytic enzyme," PNAS, vol. 98, No. 7, Mar. 27, 2001 pp. 4107–4112.

Patron, R. L., et al. "Lysostaphin Treatment of Experimental Aortic Valve Endocarditis Caused by a *Staphylococcus aureus* Isolate with Reduced Susceptibility to Vancomycin," Antimicrobial Agents and Chemotherapy, vol. 43, No. 7, Jul. 1999, pp. 1754–55.

Smith, H. W., et al. "Effectiveness of Phages in Treating Experimental *Escherichia coli* Diarrhoea in Calves, Piglets and Lambs," Journal of General Microbiology, 129, pp. 2659–2675, 1983.

Smith, H. W., et al. "The Control of Experimental *Escherichia coli* Diarrhea in Calves by Means of Bacteriophages, " Journal of General Microbiology, 133, pp. 1111–1126, 1987.

Soothill, J. S. "Treatment of experimental infections of mice with bacteiophages," J. Med. Microbiol., vol. 37, pp. 258–261, 1992.

Summers, William C., "Bacteriophage Therapy," Annu. Rev. Microbiol. 2001, 55, pp. 437–451.

Tvede, M., et al. "Bacteriophage for Chronic Relapsing *Clostridium Difficile* Diarrhoea in Six Patients,"The Lancet, May 27, 1989, pp. 1156–60.

Report of a WHO Expert Committee, "Salmonellosis Control: The Role of Animal and Product Hygiene, " WHO Technical Report Series 774, pp. 7–83, 1988.

Williams, Jr., L. P., et al. "Sources of salmonellas in market swine," J. Hyg. Camb., 66, pp. 281–293, 1968.

Williams, Jr., L. P., et al. "Patterns of *Salmonella* Excretion in Market Swine, " American Journal of Public Health, vol. 57, No. 3, pp. 466–471, Mar. 1967.

Wood, R. L., et al. "Distribution of persistent *Salmonella typhimurium* infection in internal organs of swine, " Am J. Vet. Res., vol. 50, No. 7, Jul. 1989, pp. 1015–1021.

\* cited by examiner

COMPOSITIONS AND METHODS FOR REDUCING THE AMOUNT OF SALMONELLA IN LIVESTOCK

This application claims priority to U.S. Provisional Patent Application No. 60/246,972 filed on Nov. 13, 2000 which is hereby incorporated by reference in its entirety.

The U.S. Government may have certain rights in this invention pursuant to Grant Number 453-40-30 from the U.S. Department of Agriculture.

BACKGROUND OF THE INVENTION

Enteric bacteria such as Salmonella and *Escherichia coli* can cause food-borne illness in humans due to ingestion of contaminated food products. The economic and health consequences of contaminated livestock increase the importance of finding an inexpensive yet effective method of reducing or eliminating food-borne illness. Concern regarding the overuse of antibiotics has lead to a search for alternative mechanisms to combat livestock-related infection.

Bacteria resistant to antibiotics are a threat to human and animal health. New classes of antibiotics have not been discovered in the past 30 years. Furthermore, antimicrobial usage in animals is being restricted in order to protect the public health. Concurrently, changes in social awareness and concerns regarding food safety have increased the need for reduced levels of Salmonella in pigs and other livestock.

Previous studies reported that the culture positive rate of Salmonella in market weight pigs gradually increases from farm to lariage, and ultimately to slaughterhouse. The sources of Salmonella contamination in pigs includes environments (transportation vehicles, holding areas, etc.), active Salmonella shedding pigs, and recurrent Salmonella shedding among carriers because of stress during transport or delivery. Healthy pigs become Salmonella culture positive in tissue samples within as few as three hours after infection resulting from exposure to Salmonella infected pigs. No matter what the sources of Salmonella infection into market weight pigs, the rapid dissemination of Salmonella in pigs prior to slaughter is an important risk factor in pork product contamination.

Bacteriophage resemble human and animal viruses in a number of ways. For example, viruses infect specific cell types and can cause extensive damage to the infected cells. In animals, this can lead to the production of diseases. Likewise, phages have specific bacterial targets and can cause extensive damage to the bacteria. Lytic bacteriophage are a particularly efficient killing machine for bacterial cells. Lytic bacteriophage initially contact their hosts through specific receptors in their tail followed by injection of their DNA into the host bacterial cell. Like a "Trojan Horse," once inside the cell they direct the production of quantities of progeny phage that are released when the bacterium is lysed and killed by the phage. Lytic phages continue to proliferate in an animal as long as bacteria are present to be infected by the phage.

Experimentally, phage have been shown to reduce diarrhea and the numbers of *Escherichia coli* in the intestine of piglets. Smith, H. W. and Huggins, M. B., Effectiveness in Treating Experimental *Escherichia coli* Diarrhea in Calves, Piglets and Lambs, Journal of General Microbiology 129:2659-75 (1983). Phages lytic for *Salmonella typhimurium* were found to reduce the levels of Salmonella in both the digestive tract and liver of day-old chicks. Berchieri et al., The Activity In The Chicken Alimentary Tract Of Bacteriophages Lytic For *Salmonella typhimurium*, Res. Microbiol., 142:541-549 (1991). Research publications and review articles regarding phage have identified various problems, misconceptions, and pitfalls associated with their use as therapeutics. Of particular concern is the selection of resistant bacteria through long-term use of bacteriophage treatment. Resistant bacteria may be a more significant health threat than the initial disease if antibiotics or other bacteriophage are not available to treat the resistant organisms.

Because the reduction of Salmonella in livestock prior to slaughter can reduce the prevalence of food-borne human salmonellosis, there has been much interest in developing pre-harvest reduction strategies against Salmonella. Despite many studies, an effective strategy to control Salmonella in livestock has not previously been found.

SUMMARY

This invention provides compositions comprising Felix 0-1 Phage (F01 phage) in an acceptable carrier and methods of using the compositions to reduce the amount of Salmonella in livestock and meat products. The present inventors have found that the F01 phage significantly reduces Salmonella in livestock. One embodiment of the invention provides a composition for reducing the amount of Salmonella in a livestock animal comprising a Salmonella reducing effect amount of the F01 phage in an acceptable carrier.

Also provided herein are methods of reducing the amount of Salmonella in a swine prior to shipment by administering a composition containing F01 phage, in an acceptable carrier to swine from about 24 hours to less than about 3 hours prior to harvest of the swine, in an amount effective to reduce the amount of Salmonella in the swine.

Additional embodiments of the present invention will be set forth in part in the description that follows, and in part will be obvious from the description, or may be learned through the practice of the invention. The objects and advantages of the invention will be attained by means of the instrumentalities and combinations particularly pointed out in the appended claims.

DETAILED DESCRIPTION OF THE INVENTION

Figure 1:
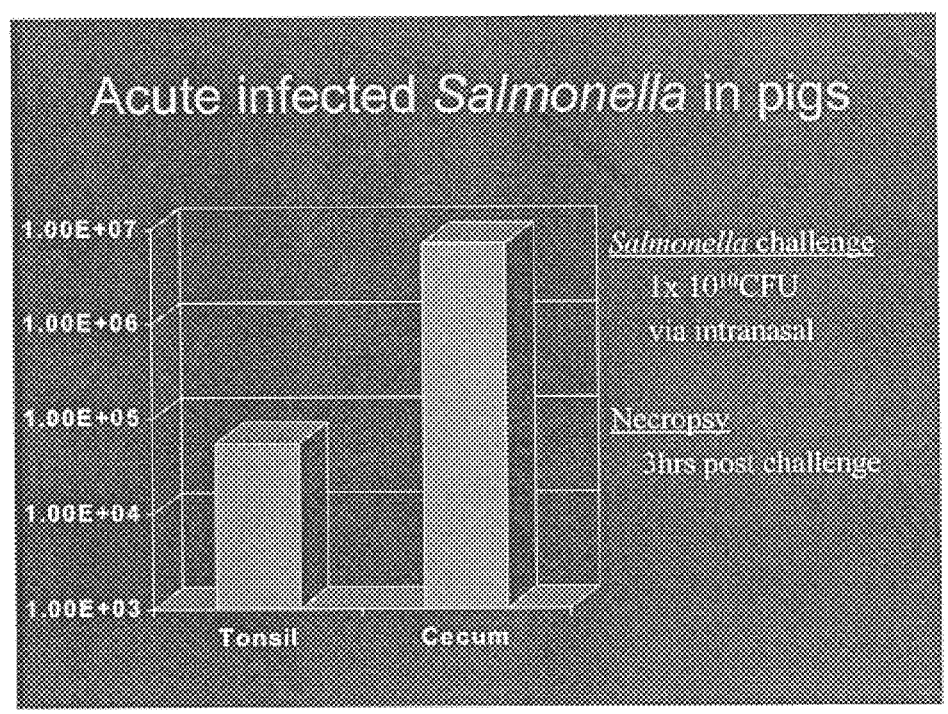
FIG. 1 shows the extent of Salmonella infection in the tonsil and cecum of pigs 3 hours post infection with *Salmonella typhimurium*.

Salmonella can disseminate into the body organs of livestock within a few hours after infection. Livestock susceptible to Salmonella infection are at greatest risk when confined with other animals as they are moved from farm to lariage, and ultimately to the slaughterhouse. Thus, Salmonella-negative livestock may be infected through transport and holding in the lariage just prior to slaughter. Rapid dissemination of the Salmonella results in a greatly increased risk of contaminated meat products. A pre-harvest intervention strategy that uses F01 phage to reduce the rapid dissemination of Salmonella and, concomitantly, the potential for selection of resistant Salmonella strains in livestock prior to slaughter, reduces the prevalence of food-borne salmonellosis in humans via the ingestion of Salmonella contaminated products.

One embodiment of the invention provides a composition comprising a Salmonella reducing effective amount of F01 phage (available from, for example, the Salmonella Genetic Stock Center, University of Calgary, Alberta, Canada) in an acceptable carrier (e.g., physiological saline, water, animal feed, Luria broth ("LB")). F01 phage is a well characterized Salmonella specific bacteriophage previously used to characterize and type Salmonella strains. See e.g. Macphee et al., Journal of General Microbiology 1975, 87:1-10; Lindberg, A. A., Journal of General Microbiology 1967, 48:225-233.

Compositions containing F01 phage can be provided in a variety of dosage forms (e.g., oral, injectable, aerosol, rectal). Oral dosage forms include F01 phage formulated in, for example, animal feed, water, bacterial media (e.g., LB), and saline. Injectable dosage forms include F01 phage formulated in, for example, saline and water. Aerosol dosage forms include F01 phage formulated in water or saline and combined under pressure with a suitable propellant. Rectal dosage forms include F01 phage combined in a suppository formulation. Other dosage forms include tablets and capsules for oral administration and creams, lotions, gels, and transdermal patches for topical administration.

The F01 phage has lytic activity against at least twelve strains of Salmonella as shown in Table 2.

TABLE 2

Lytic (killing) activity of Felix 0-1 phage against Salmonella spp by spot test

| Salmonella strain | lytic activity | Salmonella strain | lytic activity |
|---|---|---|---|
| S. typhimurium x4232 | ++ | S. heidelberg | ++ |
| S. typhimurium (cophenhagen) | ++ | S. infantis | ++ |
| S. typhimurium DT 104 | ++ | S. muenchen | + |
| S. agona | + | S. newport | + |
| S. choleraesuis | ++ | S. thompson | ++ |
| S. derby | + | S. worthington | + |

++: complete confluent lysis
+: incomplete confluent lysis
−: no effect

Salmonella serotypes most frequently isolated from swine with clinical signs of infection include S. derby, S. choleraesuis kunzendorf, S. typhimurium, S. heidelberg, S. choleraesuis, S. anatum, S. mbandaka, and S. schwarzengrund. However, Salmonella typhimurium is the major serotype causing foodborne illness and has a wide host range, including humans. The broad host range of the F01 phage makes it especially well suited for use against various serotypes of Salmonella, including Salmonella typhimurium, in a pre-harvest intervention strategy. Use of a phage having a broad host range to Salmonella as a short term, pre-harvest intervention strategy minimizes the risk of developing Salmonella resistant bacteria. Development of Salmonella strains resistant to phage therapy is associated with previous attempts at long term phage therapy.

F01 phage can be propagated using a host strain of Salmonella (e.g., Salmonella typhimurium). For example, S. typhimuriumχ4232, a nalidixic acid resistant strain, can be used to infect swine and to propogate phages. Salmonella inoculum can be prepared by any suitable method, such as growing the bacteria in LB broth. Phage stock or lysate can also be prepared by any suitable method, such as using GCA (glycerol-Casamino acids) medium supplemented with calcium chloride, and filtered prior to use using, for example, a 0.45 micrometer filter. Phage particles can be further purified, if desired, by techniques such as precipitation with polyethylene glycol, centrifugation, and dialysis.

An exemplary Salmonella reducing effective amount of F01 phage is about $10^6$ to about $10^{12}$ plaque forming units (PFU) of F01 phage. In another embodiment of the invention, at least about $10^9$ to $10^{11}$ total PFU of F01 phage are provided in a carrier. In yet another embodiment of the invention, about $10^{10}$ PFU of F01 phage are provided in an acceptable carrier. Alternatively, phage can be lyophilized and dissolved in an acceptable carrier just prior to administration. Administration of F01 phage in a Salmonella reducing amount to a livestock animal prior to harvest will typically reduce the amount of Salmonella in the infected animal by at least about 10 to about 100,000 fold.

F01 phage can be administered to a livestock animal by a variety of routes, including, for example, oral, inhalation, nasal, intramuscular, intraperitoneal, intrathecal, vaginal, rectal, topical, and combinations thereof. F01 phage can be administered orally to an animal, for example, in a volume of about 1 to about 100 ml of a carrier. In one embodiment of the invention, phage lysate or stock can be used to replace water available for consumption by animals prior to leaving the farm, during transport, or during holding. F01 phage lysate can be provided in amounts up to about six gallons in a day depending on the size of the animal. The concentration of phage in the carrier can be adjusted to any desired level. Alternatively, F01 phage can be administered by injection in a volume of about 5 to about 50 ml of a carrier. In another embodiment of the invention, F01 phage is combined with animal feed and administered orally to an animal. The F01 phage animal feed formulation can be provided to animals at selected time intervals (as discussed below) and then replaced with regular animal feed as desired. F01 phage can also be combined with water and administered orally to an animal. Alternatively, F01 phage in an acceptable carrier, such as water or saline, may be instilled into the nose of the animal with, for example, a syringe with a nasal spray tip in a suitable volume (e.g., about 1 ml). F01 phage can also be administered in an acceptable carrier via a stomach tube in any suitable volume (e.g., about 50 ml). In yet another alternative, F01 phage can be formulated in an aerosol by combining the phage in a carrier, such as water or saline, or in a propellant (e.g., trichloromonofluoromethane, dichlorodifluoromethane, and oleic acid). Aerosol formulations of the F01 phage can administered in the nasal passage or oral cavity of the animal. F01 phage can also be administered rectally by providing the phage in a suppository.

In one embodiment of the invention, intramuscular injection of F01 phage selectively reduces the level and dissemination of Salmonella in body organs and tissue. In another embodiment of the invention, oral administration of F01 phage selectively reduces the level and dissemination of Salmonella in the gastrointestinal tract of an animal. Alternatively, F01 phage is administered by both oral and intramuscular injection routes of administration to reduce the level and dissemination of Salmonella in organ systems and within the gastrointestinal tract of an animal.

Healthy swine are exposed and susceptible to Salmonella infection when housed or transported with infected animals. Thus, intervention with F01 phage treatment following exposure to Salmonella and prior to harvest is effective in reducing the amount of Salmonella in an animal. Alternatively, treatment of animals prior to harvest will limit the risk of contamination of healthy swine by infected swine in the event the animals were exposed to Salmonella when housed with other animals or transported to the slaughterhouse.

Compositions according to the invention containing F01 phage in an acceptable carrier are preferably administered to livestock as a short-term treatment. "Short-term" refers to less than about 24 hours to about 12 hours prior to harvest, alternatively less than about 12 to about 6 hours prior to harvest or less than about 3 hours prior to harvest. In contrast to prior use of phage therapy, short term treatment minimizes the risk of developing resistant Salmonella strains.

F01 phage can be administered to animals in single or multiple doses. In one embodiment of the invention, F01 is administered to an animal in a single dose prior to harvest. Alternatively, F01 phage can be administered in 2 to 5 doses prior to harvest and after exposure of the animal to Salmonella. Each dose may contain, for example, about $10^6$ to about $10^{12}$ PFU of F01 phage. In another embodiment, a dose contains about $10^{10}$ PFU of F01 phage. When administered in multiple doses, several routes of administration may be used or combined. For example, phage can be administered in a first dose via injection followed by subsequent oral administration of the phage. Alternatively, F01 phage can be orally administered in a first dose followed by a second dose administered by injection. Any desired combination of routes of administration may be used to optimize administration of the phage and may be determined by one of ordinary skill given the teachings herein.

In another embodiment of the invention, the F01 phage is administered to animals prior to harvest and after exposure to Salmonella. As discussed above, exposure and potential exposure to Salmonella can occur at several stages of an animal's life. For example, livestock animals are exposed to Salmonella when they are housed with infected animals, ingest contaminated food or water, during transport with infected animals, or by intentional or accidental infection with Salmonella. The terms "exposed to Salmonella" and "exposure to Salmonella" also refer to animals that may have been exposed to Salmonella whether or not they actually have been exposed to Salmonella. For example, co-mingling animals potentially exposes an animal to Salmonella since animals in the co-mingled group may be infected by or carry Salmonella.

In yet another embodiment of the invention, phage are administered to an animal prior to harvest in a single dose at about 3 hours following exposure to Salmonella. In another embodiment of the invention, F01 phage are administered prior to harvest and at about hourly intervals for up to about nine hours following exposure to Salmonella. Alternatively, F01 phage are administered to an animal prior to harvest at about 3, 5, 7, and 9 hours following exposure to Salmonella. F01 phage can also be administered to an animal about an hour after exposure to Salmonella and subsequently administered at about 2 and 3 hours after exposure to Salmonella. Administering a composition comprising the F01 phage and an acceptable carrier can reduce the measurable Salmonella CFU in phage-treated livestock animals by about 10 to about 100,000 fold compared to untreated animals.

The invention also provides methods of reducing dissemination of Salmonella in livestock animals by administering a composition comprising a Salmonella reducing effective amount of F01 phage to a livestock animal after transferring livestock animals to a slaughterhouse but prior to harvest. Alternatively, F01 phage is administered to livestock animals prior to or during transfer of the animal to the slaughterhouse. The term "dissemination" refers to, for example, transmission of Salmonella from one animal to another or within a single animal.

Methods of harvesting livestock animals are also provided. The term "harvest" refers to slaughtering a livestock animal by methods accepted in the food processing industry. F01 phage is administering to livestock animals prior to harvest in an amount effective to reduce the amount of Salmonella in livestock animals followed by harvest of the animal. Alternatively, F01 phage in an acceptable carrier is administered to livestock animals at least three hours prior to harvest.

In another embodiment of the invention, F01 phage in an acceptable carrier is applied to animal meat post-harvest in order to reduce the level of Salmonella in meat products. The term "meat products" refers to any food product made from an animal (e.g., beef, poultry, lamb, pork). Acceptable carriers for the F01 phage include water, saline, and LB broth. F01 phage can be applied to the surface of the meat product to, for example, prevent contamination or to reduce the number of bacteria on the surface. Phage can be applied by, for example, spraying the surface of or soaking the meat product in a solution containing at least about $10^6$ PFU of F01 phage. F01 phage can be applied to meat products at any time following harvest (e.g., processing, curing, cutting, shipping, packaging). F01 phage solution can also be provided in a consumer product to treat surfaces and food products to reduce or prevent contamination by Salmonella. F01 phage solution can be provided in a pump or aerosol spray bottle to facilitate use of the product.

It is to be understood that the application of the teachings of the present invention to a specific problem or environment will be within the capabilities of one having ordinary skill in the art in light of the teachings contained herein. Examples of the products of the present invention and processes for their use appear in the following examples.

EXAMPLE 1

A streak of Salmonella from frozen stock was inoculated into 10 ml of TSB and incubated overnight at 37 C. After incubation, 250 microliters of innoculum was transferred to 25 ml of TSB and incubated in the shaking incubator at 37° C. until the number of Salmonella in the culture was estimated to contain $10^8$ colony forming units per ml. On the day of inoculation, pigs were withheld from feed until inoculation with either diluent or Salmonella inoculum. Pigs were manually restrained for the inoculation procedure. One ml of Salmonella inoculum or uninoculated TSB was instilled into the nose of the pig with a syringe and teflon nasal spray tip.

Tissue samples were taken from animals harvested at designated time points. The tissue samples were homogenized with a tissue grinder diluted by 10-fold in phosphate buffered saline. 100 $\mu$l of each diluted tissue sample was spread on an XLD plate containing 50 $\mu$g/ml of nalidixic acid. After incubation overnight, the numbers of Salmonella in the tissue samples were determined by the direct culture method.

EXAMPLE 2

Three week-old pigs were purchased from a Salmonella-free farm. During the one week of acclimatization at the animal facility in Iowa State University, pigs were screened for indigenous Salmonella. Salmonella-free pigs were evaluated to determine whether Salmonella rapidly disseminated after challenge with Salmonella. Pigs were intranasally challenged with *S. typhimurium* in a concentration of $10^8$ CFU (Group 1) and $10^5$ CFU (Group 2) in LB broth. Group 3 was a control group receiving only the carrier. Three hours post challenge, tonsil, liver, spleen, lung, ileocecal lymph node, and cecum contents samples were taken from sacrificed pigs and evaluated. As shown in Table 1, Salmonella rapidly disseminate to a variety of animal tissues including tonsil, liver, spleen, ICLN, and cecum, within three hours post infection with *S. typhimurium* at $10^8$ CFU but not as rapidly at $10^5$ CFU (Table 1). The data indicate that Salmonella infection in healthy market weight pigs may occur during the period from loading at the farm, transportation, holding in the lariage, and at the slaughterhouse prior to slaughter. In another experiment, five pigs were intranasally challenged with $1 \times 10^{10}$ CFU of Salmonella. When the infected pigs were sacrificed three hours post-infection, the tonsil and cecum contents had approximately $1 \times 10^5$ CFU and $1 \times 10^7$ CFU of Salmonella respectively, as shown FIG. 1.

TABLE 1

Culture positive of *S. typhimurium* in the tissues in pigs three hours post challenge with $10^8$, $10^5$ CFU of *S. typhimurium* intranasally (n = 3).

| Challenge dose | blood | tonsil | liver | spleen | lung | ICLN | cecum | feces |
|---|---|---|---|---|---|---|---|---|
| $1 \times 10^8$ CFU | 0/3 | 2/3 | 2/3 | 2/3 | 0/3 | 2/3 | 3/3 | 1/3 |
| $1 \times 10^5$ CFU | 0/3 | 3/3 | 0/3 | 0/3 | 0/3 | 1/3 | 2/3 | 0/3 |
| Control | 0/3 | 0/3 | 0/3 | 0/3 | 0/3 | 0/3 | 0/3 | 0/3 |

EXAMPLE 3

Salmonella-specific lytic Felix 0-1 phage (Salmonella Genetic Stock Center, University of Calgary, Canada) were assessed for lytic activity against various Salmonella serotypes. Phage stock was prepared by GCA medium supplemented with $CaCl_2$, filtered (pore size 0.45 um) and stored at 4° C. until used. The lytic activity of the F01 phage was assessed using the spot test on the Salmonella serotypes listed in Table 2. Briefly, one drop of phage ($1 \times 10^8$ PFU/ml) lysate was dropped on the lawn grown Salmonella spp on TSA agar plates. After culture at 37° C. overnight, the spot was observed for lytic activity (Table 2). As shown in Table 2, F01 phage has lytic activity against a wide variety of Salmonella serotypes.

A phage pool containing 26 isolated phages was used to determine if a phage pool would reduce Salmonella levels in Salmonella infected pigs. Phages were isolated from swine farms, and a human waste facility by enrichment method using *S. typhimurium* χ4232 as a target strain (Adams, M. H. 1959. Bacteriophages. Interscience Publishers, N.Y.). Each phage stock was prepared by GCA medium supplemented with $CaCl_2$. Phage lysate was filtered (pore size 0.45 m) and stored at 4° C. until used. The isolated 26 phages were pooled together in the concentration of $10^9$ PFU.

Pigs were assigned into four groups (five animals per group): phage untreated positive control and three groups where each was treated with phage cocktail by a different route of administration: intramuscular treatment (IM), intraperitoneal treatment (IP), and oral treatment (Oral). Pigs in all groups were intranasally challenged with *S. typhimurium* at $1 \times 10^8$ CFU. Eighteen hours post challenge, pigs in all phage treatment groups received the phage cocktail consisting of 26 isolated phage in the concentration of $1.2 \times 10^9$ PFU via IP, IM and oral routes, respectively. Twenty-four hours post phage treatment, two animals in each group were sacrificed. The remaining three animals were then sacrificed at 48 hours post phage treatment. Tonsil, mesenteric lymph node (MLN), ileum content, cecal content, blood, liver, lung, and spleen samples were taken. The level of Salmonella in the samples was quantitated by direct culture on XLD (Salmonella selective) agar plates with 50 ug/ml of nalidixic acid. As shown in Tables 3 and 4, treatment with the pool of 26 isolated phages was not effective in reducing or preventing dissemination of Salmonella.

TABLE 3

The population of *S. typhimurium* in tissues samples at 24 hours after phage pool ($1 \times 10^{10}$ PFU) treatment into the pigs challenged with *S. typhimurium* ($5 \times 10^8$ CFU) before phage treatment. Phage pool consisted of 26 isolated phages. The numbers indicate the number of *S. typhimurium* per gram of samples.

| group 24 h pi* (n = 2) | blood | tonsil | liver | spleen | lung | ileum | MLN | cecum | feces |
|---|---|---|---|---|---|---|---|---|---|
| untreated | <$10^2$ | NT | <$10^2$ | <$10^2$ | <$10^2$ | $1.8 \times 10^4$ | $1.3 \times 10^4$ | $1.5 \times 10^4$ | $2.9 \times 10^4$ |
| intraperitoneal | <$10^2$ | $1.4 \times 10^4$ | <$10^2$ | <$10^2$ | <$10^2$ | $4.5 \times 10^4$ | $1.0 \times 10^{2\dagger}$ | $9.5 \times 10^4$ | $1.6 \times 10^5$ |
| intramuscular | <$10^2$ | $9.6 \times 10^2$ | <$10^2$ | <$10^2$ | <$10^2$ | $6.1 \times 10^3$ | $2.1 \times 10^4$ | $5.0 \times 10^4$ | $5.0 \times 10^5$ |
| oral treatment | <$10^2$ | $9.9 \times 10^3$ | <$10^2$ | <$10^2$ | <$10^2$ | $3.5 \times 10^{1\dagger}$ | $3.1 \times 10^4$ | $8.0 \times 10^4$ | $5.0 \times 10^3$ |

<$10^2$: minimum limit to detect the number of bacteria in the samples.
*Post inoculation with phage pool
†Phage treatment showed the partial effect dependent on the administration route of phage pool

TABLE 4

The population of S. typhimurium in tissues samples at 48 hours after phage pool
($1 \times 10^{10}$ PFU) treatment in the pigs challenged with S. typhimurium ($5 \times 10^8$ CFU). The
Phage pool consisted of 26 isolated phages. The numbers indicate the number of S.
typhimurium per gram of samples.

| group 48 h pi* (n = 3) | blood | tonsil | liver | spleen | lung | MLN | cecum | feces |
|---|---|---|---|---|---|---|---|---|
| untreated | $<10^2$ | $5.4 \times 10^4$ | $<10^2$ | $<10^2$ | $<10^2$ | $1.0 \times 10^4$ | $1.0 \times 10^4$ | NT |
| intraperitoneal | $<10^2$ | $1.3 \times 10^4$ | $<10^2$ | $<10^2$ | $<10^2$ | $7.7 \times 10^3$ | $4.9 \times 10^4$ | $5.6 \times 10^4$ |
| intramuscular | $<10^2$ | $4.9 \times 10^4$ | $<10^2$ | $<10^2$ | $<10^2$ | $3.5 \times 10^3$ | $8.7 \times 10^2$ | $6.7 \times 10^3$ |
| oral treatment | $<10^2$ | $4.1 \times 10^4$ | $<10^2$ | $<10^2$ | $<10^2$ | $7.2 \times 10^3$ | $1.6 \times 10^4$ | $5.4 \times 10^4$ |

$<10^2$: minimum limit to detect the number of bacteria in the samples.
*Post inoculation with phage pool

EXAMPLE 4

Five three week-old pigs each were assigned to a Salmonella positive control group and a phage treatment group. Pigs were intranasally challenged with $5 \times 10^8$ CFU S. typhimurium. Pigs in the phage treatment group received 10 ml of $2 \times 10^{10}$ PFU of Felix 0-1 phage via oral and IM routes of administration at three hours post infection. The pigs in the Salmonella positive control received an equivalent volume of carrier vial oral and IM routes of administration three hours post infection. At nine hours post infection with Salmonella, all pigs in both groups were sacrificed and tissue samples were removed for analysis. The level of Salmonella in tissue samples was quantitatively enumerated by direct culture method on XLD agar plate with 50 ug/ml of nalidixic acid.

Figure 2:
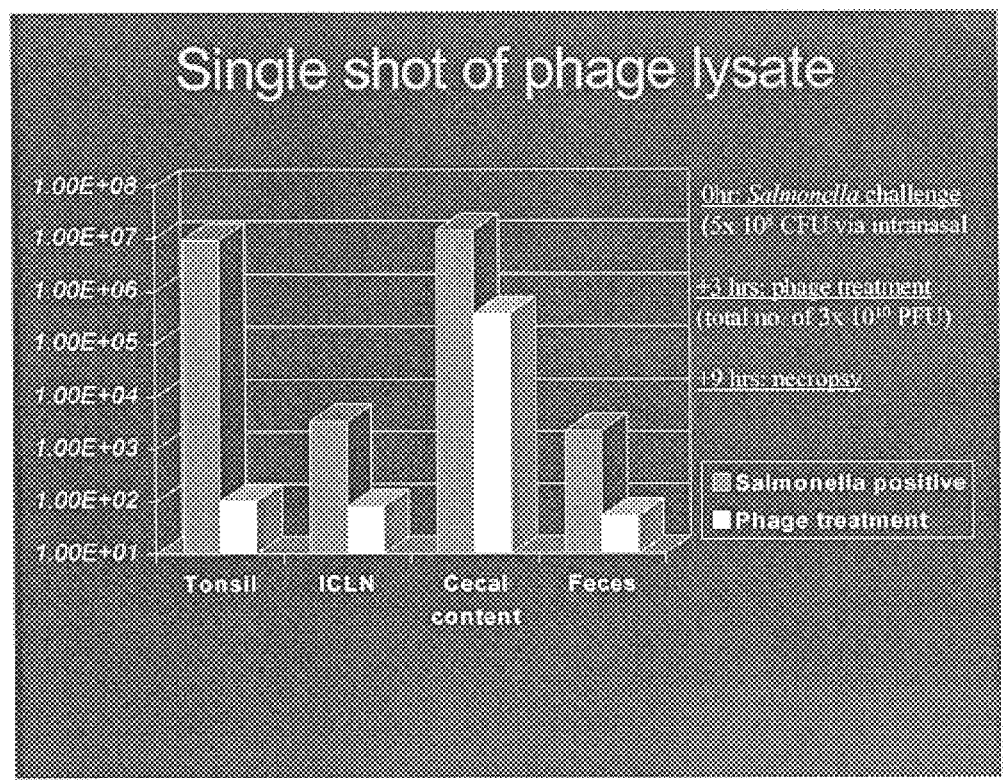
FIG. 2 shows the reduction in Salmonella in infected pigs following a single injection of F01 phage 3 hours post-infection.
Figure 3:
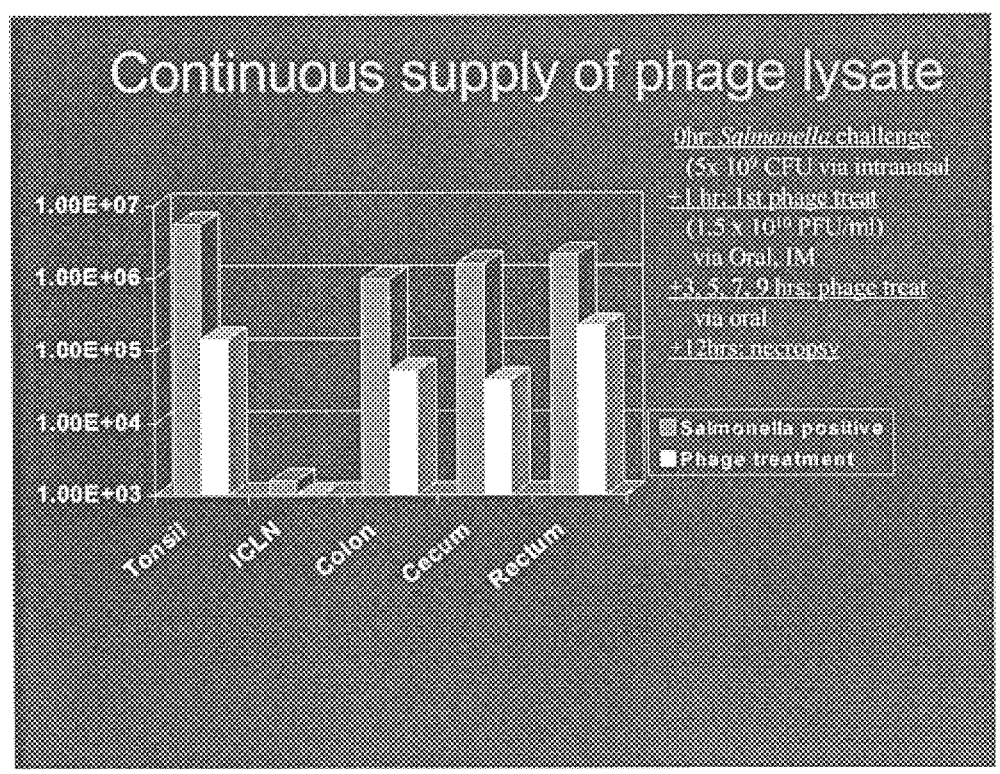
FIG. 3 shows the reduction in Salmonella in infected pigs following treatment with F01 phage at 1, 3, 5, 7, and 9 hours post-infection.

With phage treatment, the level of Salmonella in tonsil was significantly reduced by about 100,000 fold, the level of Salmonella in ICLN and feces was reduced by 10 fold, while the level of Salmonella in the cecum was reduce by about 100 fold (Table 5 and FIG. 2). Thus, a composition comprising F01 phage is effective for use in a pre-harvest intervention strategy to reduce the amount of Salmonella in livestock animals such as swine. In addition, the use of other active agents including probiotics, cytokines, antibiotics and other phage may further reduce Salmonella in livestock 3, 5, 7, and 9 hours post infection. The pigs in the control group received an equivalent volume of carrier in the volumes and at the time intervals indicated above for the phage treatment group. The level of Salmonella in tonsil was reduced by about 100 fold, while the level of Salmonella in colon, cecum, and rectum was reduced by about 10 fold (FIG. 3).

EXAMPLE 6

Figure 4:
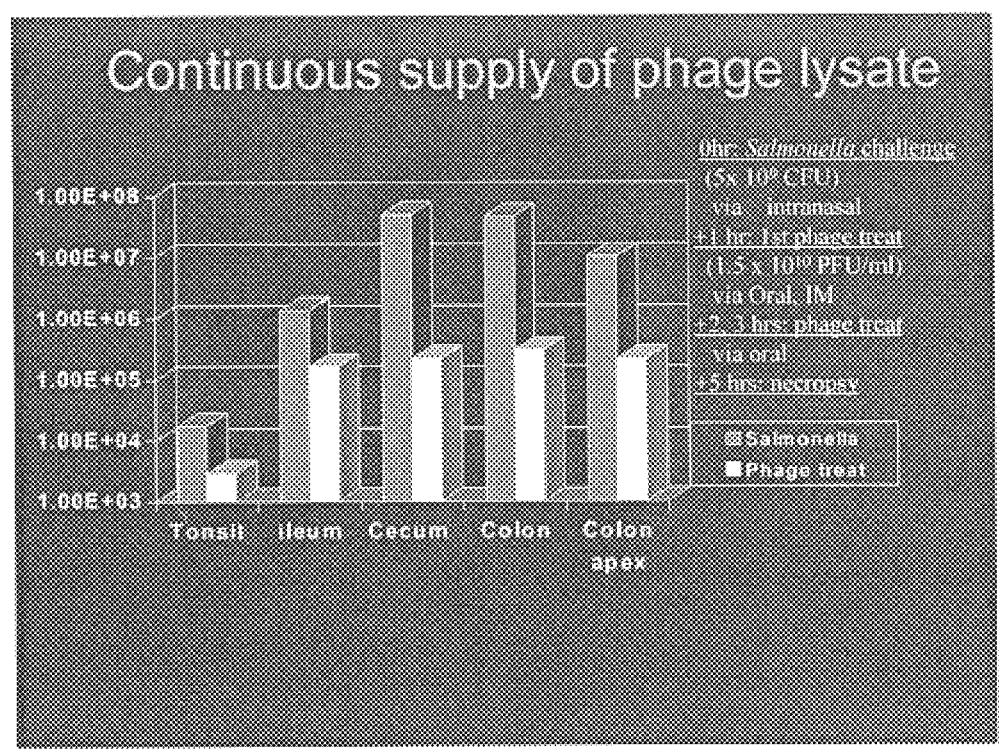
FIG. 4 shows the reduction in Salmonella in infected pigs following intermittent treatment with F01 phage at 1, 2, and 3 hours post-infection.

FIG. 4 shows the Salmonella reduction in pigs following three post-infection treatments with F01 phage. Five pigs each were assigned to a control group and a phage treatment group and intranasally challenged with $5 \times 10^9$ CFU of Salmonella. One hour post-challenge, pigs were administered $1.5 \times 10^{10}$ PFU/ml of F01 phage in 6 mls of carrier via intramuscular shot and orally administered $1.5 \times 10^{10}$ PFU/ml of F01 phage in 20 mls of carrier. The pigs were subsequently administered 15 mls of F01 phage orally at 2 and 3 hours post challenge. The level of Salmonella in tonsil and ileum was reduced by about 10 fold, while the level of Salmonella in colon, cecum, and colon apex was reduced by about 100 fold (FIG. 4).

EXAMPLE 7

Figure 5:
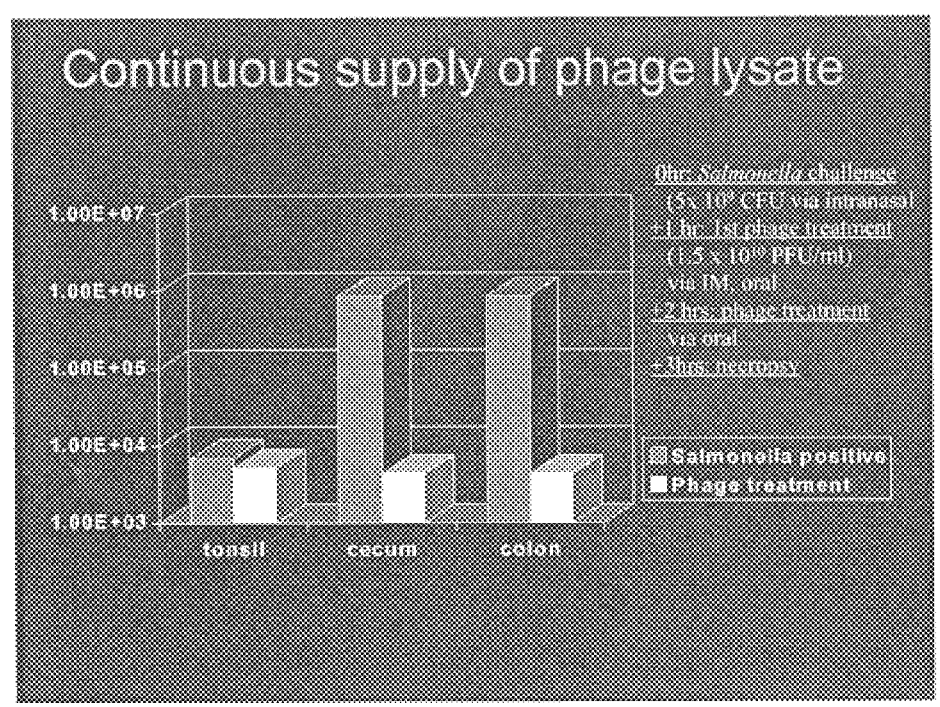
FIG. 5 shows the reduction in Salmonella in infected pigs following intermittent treatment with F01 phage at 1 and 2 hours post-infection.

FIG. 5 shows the reduction in Salmonella levels in pigs following two post-infection treatments with phage F01.

TABLE 5

The effect of Felix 0-1 phage administration ($10^{10}$ PFU) three hours post phage
treatment in pigs challenged with S. typhimurium at $5 \times 10^8$ CFU. The number of
S. typhimurium per gram of samples was counted by direct spread method.

| groups (n = 5) | blood | tonsil | liver | spleen | lung | ICLN | cecum | feces |
|---|---|---|---|---|---|---|---|---|
| untreated | $<10^2$ | $9 \times 10^6$ | $<10^2$ | $<10^2$ | $10^2$ | $3.4 \times 10^3$ | $1.4 \times 10^7$ | $2.2 \times 10^3$ |
| phage treated | $<10^2$ | $<10^{2*}$ | $<10^2$ | $<10^2$ | $<10^2$ | $2 \times 10^2$ | $3.6 \times 10^{5*}$ | $<10^2$ |

$<10^2$: It is the minimum limit to detect the number of bacteria by direct spread.
*Significant level by t-test is P < 0.001

EXAMPLE 5

Five three-week old pigs each were assigned to a Salmonella positive control group and a phage treatment group. The pigs in each groups were intranasally challenged with $5 \times 10^9$ CFU of Salmonella. One hour post-challenge, pigs in the phage treatment group were administered 6 mls of F01 phage at a concentration of $1.5 \times 10^{10}$ PFU/ml via intramuscular shot, and 20 mls of F01 phage at $1.5 \times 10^{10}$ PFU/ml orally. The pigs were subsequently administered 15 ml of F01 phage at a concentration of $1.5 \times 10^{10}$ PFU/ml orally at Five pigs each were assigned to a control group and a phage treatment group and intranasally challenged with $5 \times 10^9$ CFU of Salmonella. One hour post-challenge, pigs were administered 6 mls of F01 phage at a concentration of $1.5 \times 10^{10}$ PFU/ml via intramuscular shot and 20 mls of F01 phage orally at a concentration of $1.5 \times 10^{10}$ PFU/ml. Two hours post-infection, the pigs were administered 15 mls of F01 phage at a concentration of $1.5 \times 10^{10}$ PFU/ml orally. The level of Salmonella in cecum and colon was reduced by about 100 fold in the phage treatment group compared to the control group (FIG. 5).

EXAMPLE 8

Figure 6:
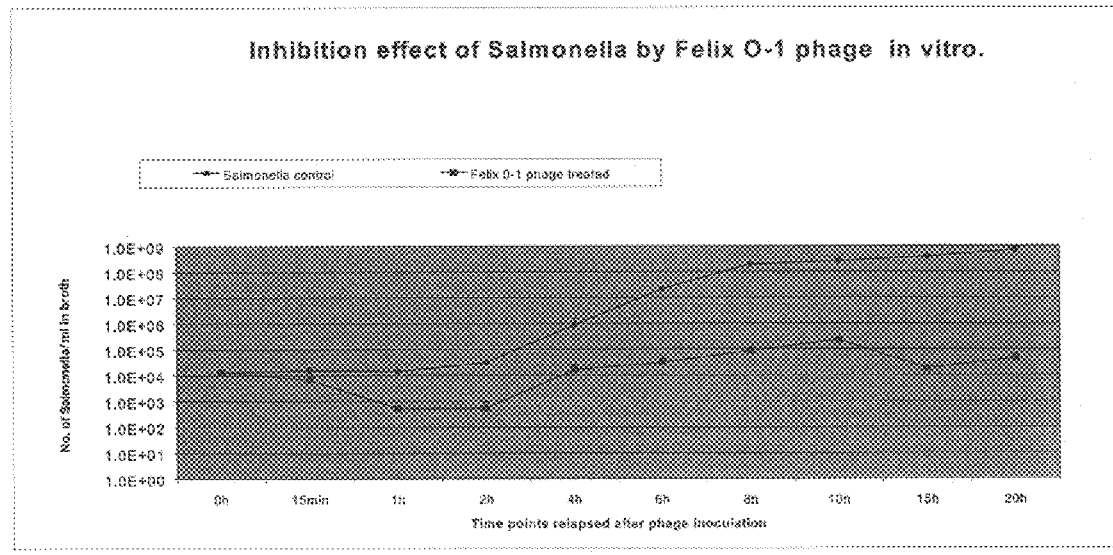
FIG. 6 shows the reduction of Salmonella in LB broth at 15 minutes, 1, 2, 4, 6, 8, 10, 15, and 20 hours after F01 phage inoculation.

FIG. 6 shows the reduction in Salmonella at various time points in broth culture following inoculation administration of the F01 phage. $1 \times 10^4$ PFU of F01 phage was inoculated into LB broth containing $1 \times 10^4$ CFU of Salmonella. While incubating at 37 C, the viable numbers of Salmonella were monitored at 15 minutes, 1, 2, 4, 6, 8, 10, 15, and 20 hours post inoculation. The level of Salmonella was reduced from about 10 fold at 1 hour to about 10,000 at 20 hours (FIG. 6).

The above description and examples are only illustrative of embodiments which achieve the objects, features, and advantages of the present invention, and it is not intended that the present invention be limited thereto. Any modifications of the present invention which come within the spirit and scope of the following claims is considered part of the present invention.

What is claimed as new and desired to be protected by Letters Patent of the U.S. is:

1. A method of reducing the amount of Salmonella in a swine prior to harvest, comprising administering a composition containing F01 phage in an acceptable carrier to said swine from about 24 hours to less than about 3 hours prior to harvest of said animal in an amount effective to reduce the amount of Salmonella in said animal.

2. The method of claim 1, wherein said carrier comprises a material selected from the group consisting of saline, water, feed, and Luria broth.

3. The method of claim 1, wherein said composition is administered from about 12 hours to about 6 hours prior to harvest of said animal.

4. The method of claim 1, wherein said composition is administered from about 6 hours to about 3 hours prior to harvest of said animal.

5. The method of claim 1, wherein said the composition is administered less than about 3 hours prior to harvest of said animal.

6. The method of claim 1, wherein said composition is administered in a single dose.

7. The method of claim 1, wherein said composition is administered in multiple doses.

8. The method of claim 1, wherein said composition is administered from 2 to 5 doses.

9. The method of claim 1, wherein said amount of Salmonella in said swine is reduced by at least 10 to about 100,000 fold.

10. The method of claim 1, wherein said composition is administered to said swine at least two times prior to harvest.

11. The method of claim 1, wherein said composition is administered orally.

12. The method of claim 1, wherein said composition is administered intramuscularly.

13. The method of claim 1, wherein said composition is administered by injection.

14. The method of claim 1, wherein said composition is administered by instillation.

15. The method of claim 1, wherein said composition is administered as a first dose and a second dose.

16. The method of claim 15, wherein said first dose is administered intramuscularly and said second dose is administered orally.

17. The method of claim 15, wherein said first dose is administered at least one hour after said swine is exposed to Salmonella.

18. The method of claim 17, wherein said second dose is administered at least one hour after said first dose.

19. A method of reducing the amount of Salmonella in a swine prior to harvest, comprising administering a composition containing at least $10^6$ PFU of F01 phage in an acceptable carrier to said swine livestock animal less than about 3 hours prior to harvest of said animal wherein said amount of Salmonella in said swine is reduced by at least 10 to about 100,000 fold.

20. A method of harvesting a livestock animal comprising administering a composition comprising F01 phage to a livestock animal after exposure to Salmonella and less than 24 hours prior to harvest of said animal in an amount effective to reduce the amount Salmonella; and harvesting said animal.

21. The method of claim 20, wherein said livestock animal is harvested at least 1 hours after administering said composition to said animal.

22. The method of claim 20, further comprising applying a composition comprising a Salmonella reducing effective amount of F01 phage to a meat product derived from said animal.

23. The method of claim 22, wherein said Salmonella reducing effective amount of F01 phage is about $10^6$ PFU.

24. The method of claim 22, wherein said meat products are selected from the group consisting of beef, poultry, lamb, and pork.

25. The method of claim 22, wherein said composition is applied by spraying.

26. The method of claim 22, wherein said composition is applied by soaking.

27. A method of reducing dissemination of Salmonella in livestock animals comprising administering a composition comprising a Salmonella reducing effective amount of F01 phage to a livestock animal from about 24 hours to less than about 3 hours prior to harvest wherein dissemination of Salmonella infection is reduced by about 10 to about 10,000 fold.

28. The method of claim 27, wherein said Salmonella reducing effective amount of F01 phage is about $10^6$ to about $10^{12}$ PFU.

* * * * *

UNITED STATES PATENT AND TRADEMARK OFFICE
CERTIFICATE OF CORRECTION

PATENT NO.     : 6,656,463 B2
DATED          : December 2, 2003
INVENTOR(S)    : Delbert L. Harris et al.

It is certified that error appears in the above-identified patent and that said Letters Patent is hereby corrected as shown below:

Title page,
Item [56], References Cited, OTHER PUBLICATIONS, "Berends, B. R., et al.," reference, should read as follows: -- "Identification and quantification of risk factors in animal management and transport regarding *Salmonella* spp. in pigs," Elsevier Science B.V. 1996, pp. 37-53. --
"McDonagh, V. P.," reference, should read as follows: -- "The Significance of the Abattoir in *Salmonella* Infection in Bradford," J. Hyg. 56:271-279, 1958.
"Tvede, M., et al." reference, "Bacteriotherapy for Chronic Relapsing *Clostridium Difficile* Diarrhoea in Six Patients," The Lancet, May 27, 1989, pp. 1156-60.
Add the following: -- International Search Report dated November 6, 2002.

Column 9,
Line 36, "reduce" should read -- reduced --.

Column 10,
Line 35, "said the" should read -- said --.

Column 12,
Line 28, "hours" should read -- hour --.

Signed and Sealed this

First Day of June, 2004

JON W. DUDAS
*Acting Director of the United States Patent and Trademark Office*